United States Patent [19]

Barwick

[11] Patent Number: 4,459,114
[45] Date of Patent: Jul. 10, 1984

[54] SIMULATION SYSTEM TRAINER

[76] Inventor: John H. Barwick, 8 Guilder La., Westport, Conn. 06880

[21] Appl. No.: 436,280

[22] Filed: Oct. 25, 1982

[51] Int. Cl.³ .......................................... G09B 00/00
[52] U.S. Cl. .................................................. 434/307
[58] Field of Search .............. 434/307, 236, 237, 320, 434/321, 308, 309, 310, 314, 247, 250, 252, 257

[56] References Cited

U.S. PATENT DOCUMENTS

| | | | |
|---|---|---|---|
| 3,145,484 | 8/1964 | Bayley | 434/257 |
| 3,158,431 | 11/1964 | Gutjahr | 434/236 X |
| 3,233,346 | 2/1966 | Cornberg | 434/307 |
| 3,401,469 | 9/1968 | Shaver et al. | 434/307 |
| 3,471,947 | 10/1969 | Genser | 434/307 |
| 3,820,133 | 6/1974 | Adorney et al. | 434/252 X |
| 3,996,671 | 12/1976 | Foster | 434/307 X |
| 4,015,344 | 4/1977 | Michaels et al. | 434/257 |
| 4,052,798 | 10/1977 | Tomita et al. | 434/307 |
| 4,094,079 | 6/1978 | Dorsett | 434/307 |

*Primary Examiner*—William H. Grieb
*Attorney, Agent, or Firm*—Lawrence Hager

[57] ABSTRACT

A method and system for teaching interpersonal communication skills and related information by a series of programmed steps involving: first, study by a trainee of a pre-recorded role model demonstration of the skill to be learned; annd secondly, the verbal interaction by the trainee with one or more audio-visually displayed target personalities, and the recording of both sides of the dialogue for subsequent review, critique, and re-recording if deemed necessary.

The simulation system trainer comprises a carrel type study station having videotape recorders, television receivers, a television camera, a control panel and accessory lighting.

15 Claims, 20 Drawing Figures

SIMULATION SYSTEM TRAINER

FIELD OF THE INVENTION

The invention relates to a method and system for effecting behavior modification with regard to specific skill areas and, more particularly, to a method and system for teaching and reinforcing skills acquisition by means of audio-visual comparative associations.

BACKGROUND OF THE INVENTION

In recent years a great deal of interest has been shown in the provision of interactive self-teaching devices. Combined audio and visual presentation devices, videotape recording and playback systems under computerized programming and direction have been developed.

Although such devices are capable of presenting information in both text and audio-visual formats, and can by the computer test the student's mastery of a given body of information, they are not capable of teaching and testing his/her ability to verbalize this information in typical situations. This deficiency had to be addressed by live role plays between the trainee and another trainee or a supervisor. However, a serious difficulty or psychological impediment arose form the direct one-on-one relationship and resulted in considerable reluctance on the part of supervisors to give the necessary time required for effective role play, as well as nervousness and insecurity on the part of the trainee in an uncomfortable situation.

PRIOR ART STATEMENT

A known method of teaching physical arts, such as dancing, is described in U.S. Pat. No. 4,015,344 issued Apr. 5, 1977 to Herbert Michaels et al. According to the method disclosed in this patent, a camera is used to record an instructor performing before a mirror to demonstrate the action to be taught, and shows a view of his back and a view of his reflection in the mirror. When the tape recording is visually reproduced on an appropriate surface, an auxiliary pupil's mirror disposed edgewise, lets a practicing pupil see his own image. Thus, the method disclosed is one of demonstrating the physical arts from the perspective of a mirror image.

Other prior art patents of interest include: U.S. Pat. Nos. 4,094,079 issued June 13, 1978 to Loyd G. Dorsett; 3,996,671 issued Dec. 14, 1976 to Richard W. Foster et al; 3,820,133 issued June 25, 1974 to Charles S. Adorney et al; 3,233,346 issued Feb. 8, 1966 to Sol Cornberg and 3,401,469 issued Sept. 17, 1968 to John A. Shaver et al.

These patents are mentioned as being representative of the prior art and other pertinent references may exist. None of the above cited patents are deemed to affect the patentability of the present claimed invention.

The present invention involves a novel combination of features combined in such a way as to afford a very efficient, cost effective, solution to the difficulties and problems encountered with the prior art, as will become apparent as the description proceeds.

For example, in contrast to the prior art, the present invention provides a behaviorally oriented teaching method and system whereby, according to a preferred form or embodiment of the invention, an audio-visual demonstration of one or more acceptable sample skill demonstration dialogues are presented between a role model(s) and a typical target personality(ies), with the trainee's visual perspective being somewhat similar to that of the target personality. In this manner, the trainee is cast in the role of an observer. When the trainee has completed his/her study, and feels sufficiently prepared, he/she can actuate the trainer to reverse the model situation, and now display the target personality such that the trainee's visual perspective is that of the previously displayed role model, i.e., facing the target personality, for conducting practice dialogue interchanges with the audio-visually displayed target personality(ies). The trainee's live responses to the target personality may be selectively recorded to enable playback for self-criticism, comparison and review according to a checklist in a coordinated, off-line workbook.

If, in the trainee's opinion, his/her performance was unsatisfactory, or capable of improvement, he/she can make another attempt, and record the result—or as many attempts as are necessary to reach an acceptable skill level.

In this manner the trainee is aided in developing an individual, flexible verbal presentation for different target personalities, problems and circumstances, while substantially eliminating the psychological impediments to learning encountered in the prior art.

SUMMARY OF THE INVENTION

A method of teaching interpersonal communication skills comprising:
audio-visually displaying a prerecorded simulated dialogue between a role model and a target personality(ies) or subject(s) such that a student-trainee can eavesdrop or witness the interaction between the role model and the subject from the perspective of a direct observer;
audio-visually displaying only the subject's portion of the dialogue generally from the visual perspective of a role model;
enabling the trainee to conduct practice presentation dialogue substantially in face-to-face interaction with the subject(s) in role substitution for the prerecorded role model;
providing the trainee with a continuous visual indicator of the amount of time available for each of the responses as the trainee is talking;
selectively recording the trainee's live response dialogue with and presentation to the subject(s);
selectively displaying the trainee's stet audio-visual response dialogue and presentation for instructive comparison and/or self evaluation;
enabling the trainee to go back to the beginning of any practice episode, and repeat the process for rerecording.

A behavior training system for teaching specific skills such as, for example, but not restricted to, selling and supervisory management, comprising:
audio-visual display means for presenting a prerecorded or simulated dialogue between a role model and a target personality;
means for selectively causing the display to present only the target personality's portion of the dialogue with the role model, said target personality being displayed in substantially front facial perspective view;
means for audio-visual recording a presentation and dialogue of a trainee in response to the target personality;
means for selectively displaying the trainee's recorded audio-visual presentation and dialogue.

a further feature of the above noted system is the incorporation or use of means such as a course workbook or computer programmed text displays for querying the trainee to effect a self-criticism and awareness of his/her achieved level of performance, knowledge and apparent confidence.

Accordingly, it is an object of the present invention to provide a method and system for teaching interpersonal communication skills and related information.

Another object of the present invention is to provide a method and system for effecting behavior modification to predetermined standards.

Another object of the present invention is to provide a method and system for teaching and/or reinforcing skills acquisition by means of audio-visual comparative association, and subsequent live practice.

Another object of the present invention is to provide a method and system of self-instruction which eliminates the psychological impediment to learning generally encountered by a trainee when being trained via role play methods by his/her supervisor or co-worker.

Another object of the present invention is to provide a method and system of learning whereby a student or job trainee can review his/her audio-visual responses to a displayed personality for self-criticism according to a predetermined set of self probing questions, and record them if desired.

Another object of the present invention is to provide a method and system for simulating typical job situations and dialogue with problem personalities as these occur in everyday sales and management applications in business, thereby reducing the need for in-the-field (on site actual contact) training by a co-worker.

Another object of the present invention is to provide a method and system for audio-visual demonstration of acceptable supervisory management skills and for simulating interpersonal dialogue with a supervisor trainee.

BRIEF DESCRIPTION OF THE DRAWINGS

Other objects and advantages of the present invention will be evident from the following detailed description when read in conjunction with the accompanying drawings which illustrate the preferred embodiments of the present invention. Similar reference numerals refer to similar parts throughout.

FIG. 1 is a perspective view of the simulation system trainer according to the present invention;

FIG. 4a is a front facial perspective representation of a first target personality being displayed on the monitor represented in FIG. 3a;

FIG. 4b is a perspective side view of a trainee observing and/or in interactive dialogue with the first target personality shown in FIG. 4a;

FIG. 5a is a front facial perspective representation of the first target personality's portion of the prerecorded dialogue depicted in FIG. 3a;

FIG. 6b is a perspective representation of a trainee observing and/or in interactive dialogue with the second target personality displayed in FIG. 6a;

DESCRIPTION OF THE PREFERRED EMBODIMENTS

Referring to the drawings in general and to FIG. 1 in particular, shown therein and referred to by the general reference number 10 is a simulation system trainer housed in an individual carrel type study station constructed in accordance with the preferred embodiment of the present invention. The simulation system trainer 10 generally includes two audio-video tape recorder/playback units 11 and 12, two television receivers or monitors 13 and 14, a television camera 15, a switch control panel or keyboard 16 and accessory lighting 17.

The carrel type study station 10 contains a main or central display unit 18, and two hinged door units 19 and 20. The door units 19 and 20 are dimensioned such that they may be folded or closed in juxtaposition with the central display unit 18 to facilitate storage and transportation of the simulation system trainer 10, while safeguarding its constituent compartmentalized components.

The door units 19 and 20 each contain compartments or alcoves for storing or mounting, for example, audio-video tape cassettes 21 and a television camera 15, respectively. The accessory lighting 17 comprises a plurality of lights, for example, mounted on each of the door units 19 and 20.

A storage compartment 22 is provided in one of the doors 20 for receiving the detachable control unit 16. The camera 15, which may comprise a conventional black and white or color camera may be hinged or pivot mounted (not shown) for ease of directing the lens and for swinging the camera 15 into storage alcove 23. In this manner, a self-contained relatively compact and portable carrel type trainer or teaching machine is provided which is transportable from office-to-office, or from division-to-division of a multi-division company, thereby potentially reducing the costs of transporting personnel for training.

Since the structural and circuit details of the individual component recorders 11 and 12, monitors 13 and 14, camera 15 and keyboard 16 may be of conventional design well known to those skilled in the art, a detailed discussion thereof will not be provided herein to avoid prolixity. Lifewise the circuit details to effect switching and other controls via keyboard 16 and lead 24 may be of conventional design.

With reference now to FIGS. 1-8, the system and method of simulation training in accordance with the present invention will now be described. FIGS. 2-7 generally illustrate the sequence of audio-visual simulated and interactive dialogues developed for use with the trainer 10.

As will become apparent from the following discussion, the trainee 25 is exposed to a sequence of programmed activities, while experiencing a feeling of being in control. In this manner, training may be accomplished according to one feature of the invention, i.e., in a non-threatening and self-paced environment whereby the psychological impediments to learning generally experienced in the prior art may be substantially reduced or eliminated.

The trainee 25 is provided with booklet or workbook 26 which contains a course outline and detailed technical and reference information relating to the subject matter being taught. Also included are self-check review points to aid in critique, as well as analytic exercises to improve understanding and facilitate verbal response.

When the trainee 25 is prepared to begin the audio-visual portion of the training program, he/she selects the corresponding assigned tape cassette 27 from the cassette storage rack 21 and inserts it into the videotape recorder/playback unit 11 (VTR) at opening 39. Assuming that the trainer 10 has been previously activated, i.e., turned-on, the trainee 25 is now ready to begin the behavior modeling segment of his/her training.

The trainee 25 is in-control of the trainer 10 via switches or keys on the control panel or keyboard 16 and/or by means of individual component auxiliary control switches 28 through 36 on the respective components.

Figure 2A:
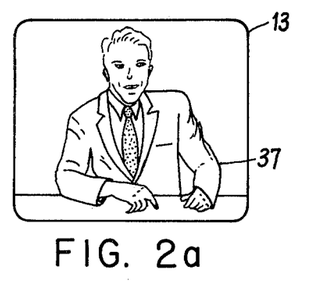
FIG. 2a is a perspective representation of a prerecorded host-narrator displayed on one of the monitors shown in FIG. 1.
Figure 2B:
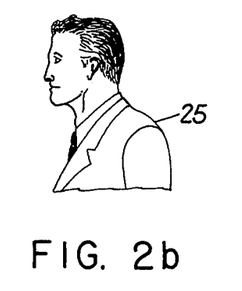
FIG. 2b is a perspective side view of a trainee observing the displayed host-narrator.

With insertion and activation of the tape cassette 27, an instructor or host-narrator 37 is audio-visually presented by means of display monitor 13 and speaker/microphone 38. The narrator 37 introduces and explains the trainer 10 and program to the trainee 25 in a relaxed and friendly mannerism and, generally emphasizes the interactive training method and purpose of the program that will be incorporated throughout. The narrator 37 is depicted or simulated on display monitor 13 as represented in FIG. 2a introducing the program, as mentioned above, in narrative dialogue such as, for example, —Hello, I am your program host and want to take this opportunity to welcome you to this training program. In the following segments, you will be presented a series of sample sales presentations being made to one or more potential customers—.

It is noted at this time that only the display monitors 13 and/or 14 of the trainer 10 are depicted in FIGS. 2 through 8 for ease of representation and understanding. It being understood that the events and interactive dialogues are taking place with the trainee 25 seated at the carrel trainer 10 as shown in FIG. 1. The trainee 25 is represented in the various steps of the interactive training method, as noted above in front of trainer 10, in FIGS. 2b, 3b, 4b, and 6b.

Following the narrator's introduction, the prerecorded tape 27 is advanced to display on monitor 13 an acceptable presentation between a role model 40 and a first potential target personality 41 (FIG. 3a) in the appropriate sales, management, or other program application context.

Figure 3A:
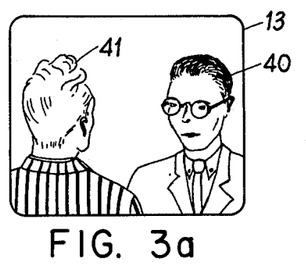
FIG. 3a is a perspective representation of a prerecorded dialogue between a role model and a first target personality.
Figure 3B:
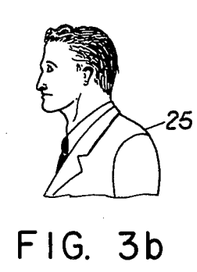
FIG. 3b is a perspective side view of a trainee observing the displayed host-narrator.
Figure 3C:
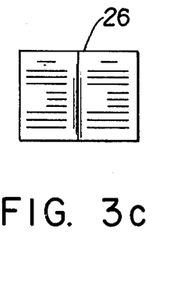
FIGS. 3c, 4c, 5c, 6c, and 7c are perspective top views of a coordinated, off-line text or workbook opened to the respective subject page corresponding to the training steps according to the invention.

The trainee's visual perspective is that of looking over the shoulder or from the side of the target personality 41, whereby the trainee 25 is able to observe the facial expressions and/or hand and body motions, if any, of the role model 40. In this manner, the trainee 25 is provided an audio-visual demonstration of how to present such information to a target (customer) personality.

The verbal responses and questions of the target personality 41 such as, for example, —Why should I purchase your product? I heard that trying to get repair can be difficult—, may be selected to prepare the trainee 25 for difficult but typical questions while demonstrating an acceptable response and interpersonal techniques by the role model 40.

The trainee 25 is then directed, either by prior course instructions or with a displayed comment on monitor 13, to review the technical and analytical questions and comments within workbook 26, or by displayed text on the television screen. For example, the trainee 25 may be asked; —Do you feel the role model should have presented statistical data to support his claim that the product is reliable—.

The trainee 25 may selectively, via keyboard 16, repeat this portion of the training program as necessary or desired to reinforce his/her knowledge of the subject information and presentation technique demonstrated by the role model 40.

During the first two steps of the program, the trainee 25 observes the audio-video tape 27 on monitor 13 as represented by FIGS. 2a, 2b and 3a, 3b. It should be noted at this time that the trainee 25 throughout the training program can selectively, via keyboard 16, stop or advance or rewind the tape 27 (and tape 43) as desired to facilitate review of tape 27 (43) and workbook 26 segments.

Figure 4A:
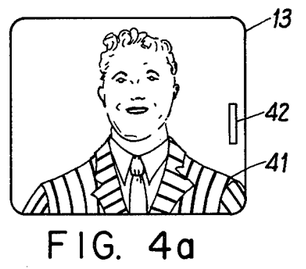
Figure 4B:
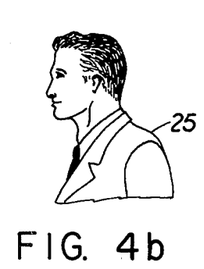
Figure 4C:
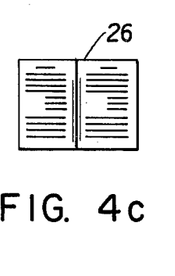

Next, the trainee 25 selectively actuates, via keyboard 16, the advance of the prerecorded tape 27 to the segment of the program where only the target personality's portion of the dialogue as depicted in the previous portion of the training tape 27 is displayed on monitor 13 as represented in FIG. 4a. The target personality 41 is displayed substantially in front-facial perspective as though addressing or directing his comments now to the (salesman) trainee 25 represented in FIG. 4b. The trainee 25 is instructed by workbook 26 and/or a monitor 13 graphic subtitles (not shown), to practice his/her interactive dialogue with the target personality 41 being simulated on monitor 13.

The trainee 25 may be paced in his/her presentation and dialogue by means of a time remaining indicator 42 such as a line which progressively becomes shorter with the passage of the trainee's alloted response period. Alternatively, an elapsed time indicator (not shown) may be presented on display 13 to aid the trainee 25, shown in FIG. 4b, to pace his/her dialogue with the simulated target (customer) personality 41 displayed on monitor 13, as shown in FIG. 4a.

With each step of the training program, the trainee 25 is requested to review the analytical questions and comments in the workbook 26. The questions etc. may be directed, for example, to aid the trainee 25 to recognize body language, or to understand his/her emotions while interacting with target personality 41, in order to develop the proper attitude for dealing with difficult and challenging remarks.

The trainee 25 as noted above, via keyboard 16, can play back the target personality's 41 segment of the tape 27, to practice mentally or aloud his/her presentation and interactive dialogue with the simulated target personality 41 represented in FIG. 4a.

When the trainee 25 feels sufficiently prepared, he/she is instructed by workbook 26 or displayed text to activate camera 15, VTR 12, and speaker/microphone 45, via keyboard 16, to record on tape 43 his/her audio-video interactive dialogue with the target personality 41 presented on monitor 13. Thus, during this portion of the training program, represented in FIGS. 4a and 4b, the trainee's 25 presentation and interactive dialogue with the simulated first target personality 41 is recorded for later analysis and review.

The trainee 25, via keyboard 16, can selectively repeat this record portion or step of the training program until he/she is satisfied with his/her performance relative to the role model 40 and review comments within workbook 26.

Figure 5A:
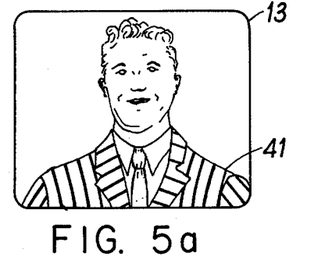
Figure 5B:
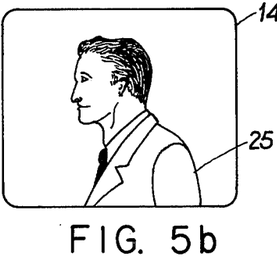
FIG. 5b is a perspective representation of the playback on a monitor shown in FIG. 1 of the trainee's dialogue recorded during the previous training step depicted in FIG. 4b.

Next, the trainee 25 is instructed by workbook 26 (FIG. 5c) to review, with activation of monitors 13 and 14, via keyboard 16 and VTRs 11, 12, the interactive and system coordinated audio-video recorded dialogues, in playback mode, between the target personality 41 and trainee 25 as represented in FIGS. 5a and 5b, respectively.

Figure 5C:
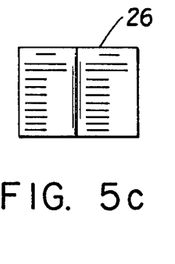

Likewise with the previous training steps, the trainee 25 is requested, either by monitor 13 or 14 graphic subtitles (not shown) or prior program outline instructions, to review the workbook's 26 analytical questions and comments, represented in FIG. 5c, such as, for example, —Did your presentation omit any points made by the role model?—, etc.

Once the basic skills have been demonstrated and practiced as discussed above, one or more different target personalities (44) may be introduced for interactive dialogue with the trainee 25. It should be noted that at this more advanced phase of the training program, the trainee 25 follows the same transactional framework, but now using his/her own ideas, and unaided by a role model's demonstration of satisfactory dialogue. In this manner, the trainee 25 is encouraged to develop an individually tailored and flexible approach to dealing with different but typical target personality traits, abilities, and preferences.

Figure 6A:
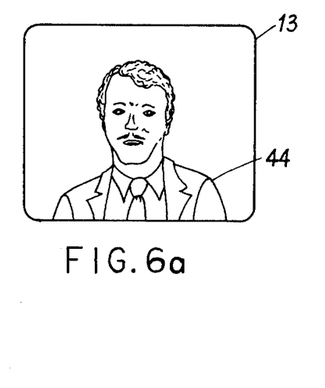
FIG. 6a is a perspective representation of a second target personality being displayed in dialogue on a monitor shown in FIG. 1.
Figure 6B:
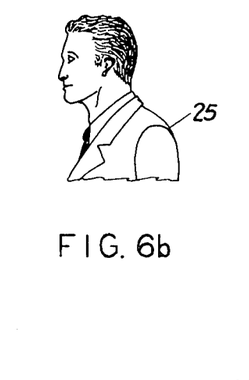

Thus, the trainee 25, represented in FIG. 6b can selectively advance the training tape 25, via keyboard 16 and VTR 11, to display a second target personality 44 and dialogue on monitor 13, as represented in FIG. 6a. Although the same subject matter and transactional framework is presented or utilized, this time a different type of personality is displayed by the target personality 44 who may also pose different questions to the trainee 25 such as, for example, —I had a great deal of trouble with your company's products in the past, so why should I buy them now?—.

The trainee 25 is assisted in understanding the problems presented by the new personality of the potential customer 44, e.g., hostility, and is given insight into overcoming this challenge with reference to workbook 26. Additionally, as a further feature of the invention, the trainee 25 may be given guidance in formulating an appropriate answer by activating, via keyboard 16, a voice-over commentary or dubbed-in suggested role model dialogue if desired by the trainee for comparison.

Figure 6C:
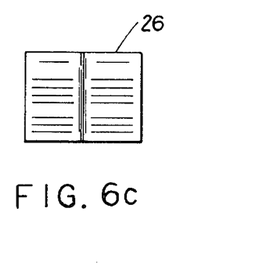

However, at this stage of the training program, the trainee 25 is assisted by exercises and checklists in the CRT displayed text or workbook 26 (FIG. 6c) to formulate/develop a personalized dialogue, based on the previously demonstrated technique and principles, without prior reference or review of a dubbed in demonstration or suggestive commentary.

As above, the trainee 25 is given the election and control, via keyboard 16, to practice this self-formulated interactive dialogue portion of the program until he/she is prepared to selectively proceed into the next recording segment or step of the training exercises.

With the trainee's 25 election to proceed, he/she activates playback of the target personality's 44 audio-visual dialogue, via keyboard 16 and VTR 11, and the record function of the trainer 10, via keyboard 16, camera 15, VTR 12 and tape 43. During playback of the target personality's 44 dialogue, (FIG. 7a), the trainee's self-formulated audio-video interactive dialogue with the simulated, via display 13 (FIG. 7a), second target personality 44 is recorded on tape 43.

Figure 7A:
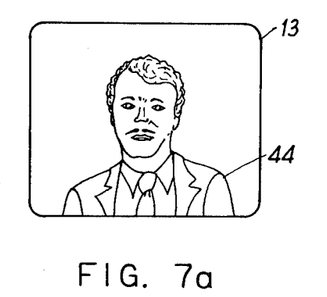
FIG. 7a is a perspective representation of the second target personality depicted in FIG. 6a in playback on the monitor.
Figure 7B:
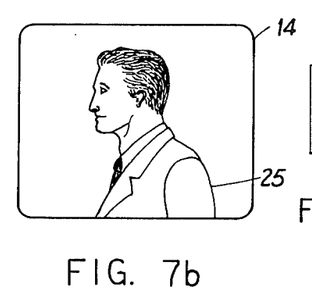
FIG. 7b is a perspective representation of the playback on a monitor shown in FIG. 1 of the trainee's dialogue recorded during the previous training step depicted in FIG. 6b.

The next step in the training program is for the trainee 25 to review his/her audio-video recorded dialogue, via monitor 14 and speaker 45, with the second target personality's 44 portion of the dialogue being correspondingly presented, via monitor 13 and speaker 38, as represented in FIGS. 7b and 7a respectively.

Figure 7C:
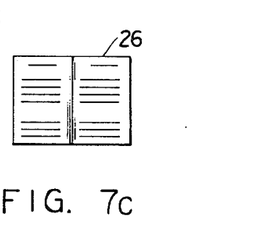
Figure 8:
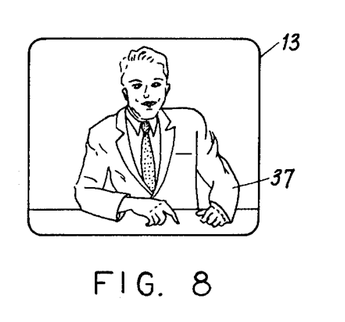
FIG. 8 is a perspective representation of the host-narrator concluding summary displayed on a monitor shown in FIG. 1.

With reference to workbook 26 (FIG. 7c) the trainee 25 is aided in constructively analyzing his/her presentation and dialogue with the second target personality 44. For example, the trainee 25 may be asked to evaluate his/her performance, and to describe his/her expressions made during the recorded dialogue with the second target personality 44.

It is emphasized at this time that a plurality of target personalities and varied questions can now be introduced in similar manner as discussed above, to maximize the trainee's learning exposure.

Following these interactive dialogues and workbook 26 review sessions, the host-narrator 29 is again presented on display 13 (FIG. 8) to reemphasize and summarize important points relative to the subject technical information and specific behavior skills being taught.

A further feature of the invention is the provision of a trainee's selected recorded dialogue for joint review with his/her supervisor or manager. In this manner a performance/instructional review may be effected whereby the trainee can be readily and objectively shown his/her strong and weak skill points while at the same time being given the opportunity to express his/her comments and feelings.

The supervisor can propose remediation or advancement based on tangible evidence of ability to perform, in the form of the trainee's recorded responses.

Figure 9:
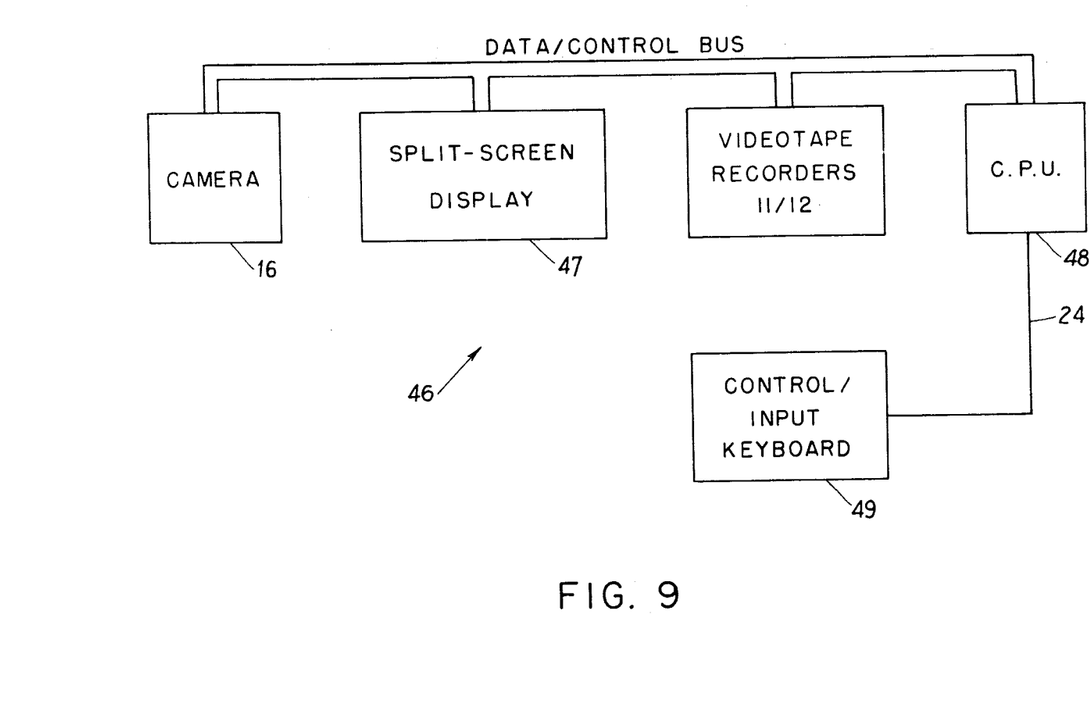
FIG. 9 is a block diagram of a second embodiment of the simulation system trainer shown in FIG. 1.

With reference now to FIG. 9, a block diagram of an alternative embodiment of the trainer/system according to the present invention is shown. The trainer/system 46 is similar to the trainer/system 10 shown in FIG. 1 with the exception that a splitscreen monitor 47 and central processing unit or computer (CPU) 48 are incorporated into the training system and method.

With appropriate software, the trainer/system 46 can be utilized to partially automate and expand the training method discussed above. For example, under CPU control, prior to and/or following each audio-video record and playback segment of the program, all the prerecorded portions of the program may be presented on the display monitor 47. However, instead of being stored on videotape in a videorecorder, as previously, these prerecorded portions are now stored in a videodisc player, and are selectively displayed as activated by the CPU. Such pre-recorded displayed portions could include, but are not restricted to: Narrator's introductory comments; any other supplementary audio-visual material; all text information, questions, exercises, and instructions formerly contained in the workbook or other printed material; role model skill demonstrations; target personalities displayed for verbal interaction by the trainee; the narrator's concluding summary. Numerous software logic branches and subroutines may be utilized to vary the difficulty level of the questions, dialogue of the target personality(ies) and rate of training depending on the trainee's inputted responses, via keyboard 49.

While certain specific embodiments have been set forth for the invention for the sake of illustration to persons skilled in the art, it is not intended to be limitative. For example, although the specific embodiments comtemplate a carrel type trainer, other formats can be utilized.

I claim:

1. An interactive behavior modification training system for teaching specific interpersonal communication skills, comprising:
    means for presenting a prerecorded audio-visual dialogue between a role model and a second personality;
    means for selectively controlling the presenting means to effect a presentation only of the prerecorded audio-visual dialogue portion of said second personality;
    means for selectively recording live interactive dialogue of a third personality with the displayed pre-recorded audio-visual dialogue of said second personality; and
    means for selectively presenting both the recorded audio-visual interactive dialogues of said second personality and said third personality.

2. A behavior modification training system as in claim 1, wherein:
    the means for presenting the prerecorded dialogue comrpises an audio-video tape recorder operatively connected to a television monitor.

3. A behavior modification training system as in claim 1, wherein:
    the controlling means comprises a switch for advancing the prerecorded dialogue to a portion containing a prerecorded simulation of said second personality directing dialogue to said third personality being disposed at the prerecorded dialogue presenting means.

4. A behavior modification training system as in claim 1, where:
    the recording means comprises a camera and an audio-video tape recorder in operative coupling therewith.

5. A behavior modification training system as in claim 1, wherein:
    the constituent component means are organized within a carrel modular training unit.

6. A behavior modification training system as in claim 1, wherein:
    the prerecorded presenting means displays said role model substantially from a front-facial perspective, while displaying substantially a perspective back view of said second personality.

7. A behavior modification training system as in claim 6, wherein:
    the controlling means causing advance of the prerecorded dialogue whereby said second personality is displayed visually substantially from a front-facial perspective directing said dialogue previously presented without said role model dialogue portion being interposed therewith.

8. A behavior modification training system as in claim 1, including:
    the presentation substantially from a front-facial perspective of one or more different simulated personalities in role substitution of said second personality.

9. A behavior modification training system as in claim 1, including:
    means for presenting information corresponding with one or more portions of the training system and dialogues being presented thereby.

10. A behavior modification training system as in claim 9, wherein:
    the information presenting means comprises a printed workbook, or other audio-visual display means.

11. A behavior modification training system as in claim 9, wherein:
    the information presenting means includes a preprogrammed computer for selectively presenting information and/or questions and/or varied dialogue of said second personality or said different simulated personalities.

12. A system for the dissemination of information to and behavior modification of an individual, the combination comprising:
    audio-video display means:
    a prerecorded audio-video subject means for being presented by said audio-video display means, said subject means including a first simulated host-narrator dialogue for explaining the system and program, a second simulated audio-video dialogue between a role model and a target personality visually displayed from a first perspective, a third simulated audio-video dialogue of said target personality's audio subject content portion of the second simulated dialogue while displaying said target personality from a second visual perspective:
    audio-video recording means for selectively recording said individual while being in interactive dialogue with said third simulated audio-video dialogue of said target personality; and
    printed information means corresponding to one or more predetermined portions of said prerecorded audio-video subject means for being reviewable by said individual.

13. A system for the dissemination of information to and behavior modification of a trainee, the combination comprising:
    at least one prerecorded audio-video tape means with dialogue thereon containing a selected subject matter information and having a format generally comprising a narrator for explaining the program steps and function, an interactive dialogue between a role model in facial perspective and a first target personality in a back or side view perspective, said first target personality being recorded in facial perspective view with an audio dialogue similar to the interactive dialogue without said role model's portion thereof, a second target personality being recorded from a facial perspective in dialogue directed generally to said selected subject matter information, and said narrator being again recorded in dialogue for emphasizing predetermined specifics of the selected subject matter information;

an audio-video trainer means having a housing including a central body and a first and a second door member each pivotally mounted to a respective corner portion of said central body and being disposable to an open disposition for forming a carrel type study station, said central body contains a first and second video display device and a first and a second videotape recorder each being operatively connected with a respective one of said video display devices, said first door member having a first storage alcove for receiving said tape means therein for storage and a first illumination source means, said second door member having a second storage alcove containing an outwardly pivotally mounted camera therein and a third storage alcove and a second illumination source means, said video camera being operatively connected with said second video tape recorder;

an audio-video tape means operatively insertable into said second videotape recorder;

a control keyboard means operatively connected with said audio-video trainer for selective control thereof by the trainee; and a workbook containing predetermined instructions and commentary concerning said selected subject matter information reviewable by the trainee;

whereby the trainee can selectively review each portion of said prerecorded audio-video tape means subject matter information and a corresponding workbook instruction and commentary pertaining thereto, and can selectively record his/her interactive audio-video dialogue with said first and second target personalities sequentially displayed on said first video display device, for later review and comparison with or without display of the respective first and second target personality interacted in dialogue with the trainee being again and correspondingly displayed on said first video display device.

14. A method of teaching verbal behavior and interpersonal communicative skills to a trainee, comprising:

audio-visual displaying a prerecorded interactive dialogue between a role model and a target personality to enable the trainee to observe the interactive dialogue;

enabling the trainee to selectively review commentary generally pertaining to said interactive dialogue;

audio-visual displaying the interactive dialogue portion of said target personality without the interactive dialogue portion of said role model being integrated therewith;

enabling the trainee to selectively review commentary generally pertaining to the interactive dialogue portion of said target personality;

enabling the trainee to practice his/her own interactive dialogue with the interactive dialogue portion of said target personality being audio-visually displayed, whereby the trainee is cast generally in role substitution for said role model;

enabling the trainee to selectively review commentary generally pertaining to his/her interactive dialogue;

recording the trainee while in interactive dialogue with the interactive dialogue portion of said target personality;

audio-visual displaying the interactive dialogue portion of said target personality and the recorded interactive dialogue of the trainee in correlative association;

enabling the trainee to selectively review commentary generally pertaining to his/her interactive dialogue;

audio-visual displaying an interactable dialogue of a second target personality;

enabling the trainee to review commentary generally pertaining to the interactable dialogue of said second target personality;

enabling the trainee to practice developing his/her own interactive dialogue with the interactable dialogue of said second target personality;

recording the trainee while in interactive dialogue with the displayed interactable dialogue of said second personality;

audio-visual displaying the interactable dialogue of said second target personality and the recorded interactive dialogue of the trainee in correlative association for review by the trainee;

enabling the trainee to review commentary generally pertaining to his/her recorded interactive dialogue with said second target personality; and reviewing a selected recorded interactive dialogue of the trainee with a supervisor.

15. An interactive behavior modification training system for teaching specific interpersonal communication skills comprising:

means for presenting a pre-recorded audio dialogue between a role model and a second personality;

means for selectively controlling the presenting means to effect a presentation only of the pre-recorded audio dialogue portion of said second personality;

means for selectively recording live interactive dialogue of a third personality with the displayed pre-recorded audio dialogue of said second personality; and means for selectively presenting both recorded audio interactive dialogues of said second personality and said third personality.

* * * * *